United States Patent [19]
Feng

[11] Patent Number: 5,467,508
[45] Date of Patent: Nov. 21, 1995

[54] TIGHTENING-UP BELT

[76] Inventor: Le-Jang Feng, 1 Fl., No. 22-10, Lane 50, Tien Mu E. Rd., Taipei, Taiwan

[21] Appl. No.: 324,941

[22] Filed: Oct. 18, 1994

[51] Int. Cl.$^6$ ................................................. A44B 11/00
[52] U.S. Cl. ..................... 24/68 SK; 24/3.3; 24/70 SK; 24/170; 24/191
[58] Field of Search ................................ 24/68 SK, 70 SK, 24/71 R, 71 SK, 498, 170, 191

[56] References Cited

U.S. PATENT DOCUMENTS

| | | | |
|---|---|---|---|
| 2,648,255 | 8/1953 | Pendleton | 24/3.3 |
| 2,779,077 | 1/1957 | Kline | 24/191 |
| 2,819,650 | 1/1958 | Seron | 24/3.3 |
| 2,926,408 | 3/1960 | Smith | 24/191 |
| 3,808,645 | 5/1974 | Chow | 24/71 SK |
| 4,683,620 | 8/1987 | Valsecchi et al. | 24/68 SK |
| 5,045,006 | 9/1991 | Sperzel et al. | 24/68 SK |
| 5,181,280 | 1/1993 | Bachry, Jr. | 24/170 |

Primary Examiner—Victor N. Sakran
Attorney, Agent, or Firm—Pro-Techtor International

[57] ABSTRACT

The present invention is related to a structure of tightening-up belt which comprises two belts, two holding-down plates and an embowed assembly plate, wherein the two sides of embowed assembly plate are provided with a slot and a shaft respectively, each of these two belts fas a plurality of check strips, the fixed ends of these two belts are pivotally fixed on two sides of a frame of the article to be used, and the free ends thereof pass through the slots on the two sides of the embowed assembly plate to be reversely folded around the shaft; each of two sides of the embowed assembly plate is provided with a holding-down plate capable of tightening or lossening the reversely-folded belts, thus the length of the tightening-up belt as a whole composed of two separate belts is adjustable, the tightening-up belt can be tightened through pulling the two belts toward two outer sides from the position where the two belts are connected, the tightness adjusting operation is handy and quick, and the tightening force thereof can be quickly and averagely conveyed to various positions of lightening-up belt to let the user feel wearing comforatble; and the reversely-folded portion (reversely-folded belt) is at the center, namely the rear side of the user's wearing position when he wears same, and will never affect the disposition of other equipment on the lateral sides of the tightening-up belt.

4 Claims, 4 Drawing Sheets

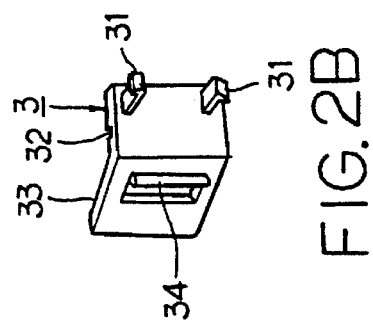
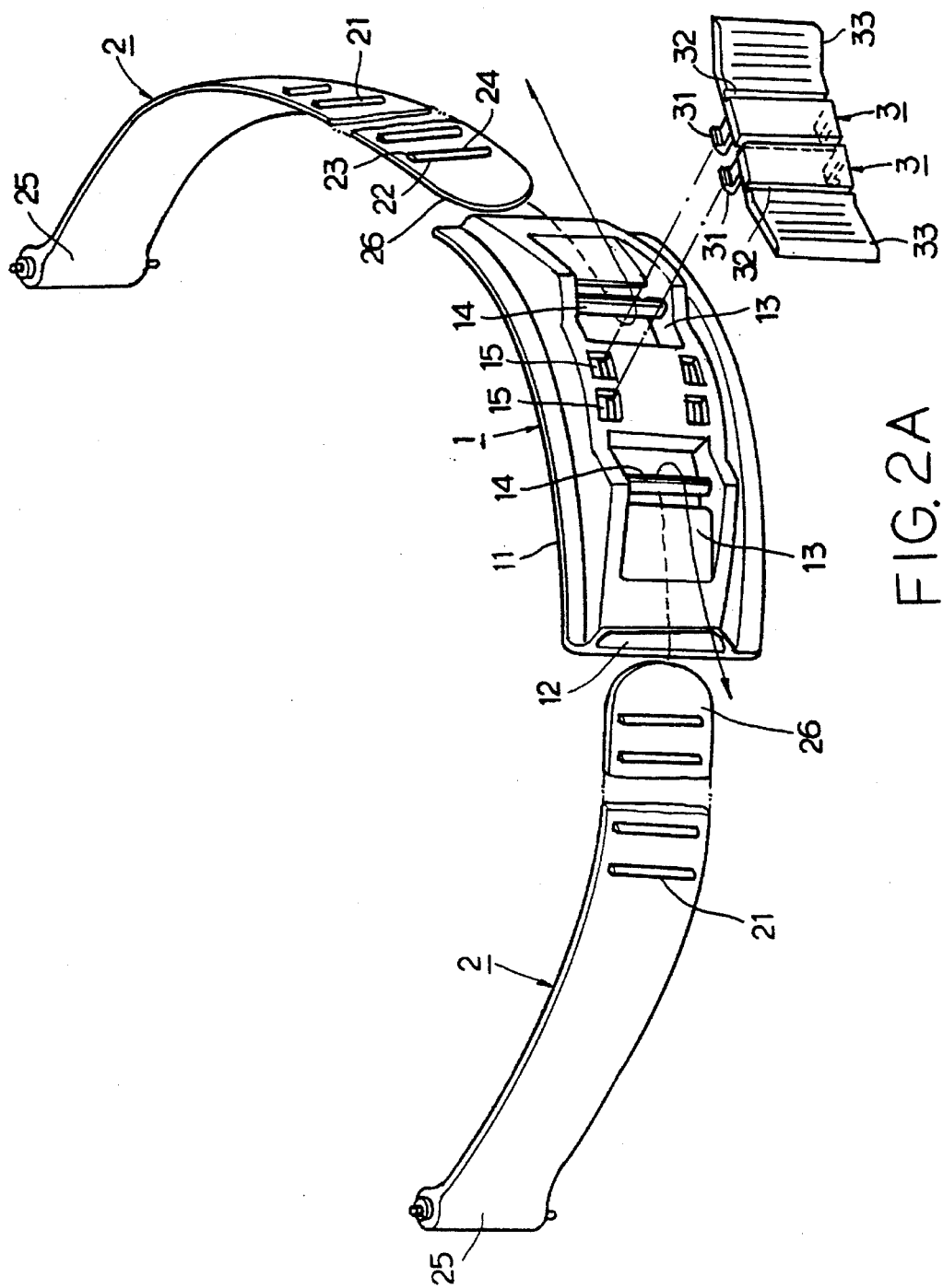

TIGHTENING-UP BELT

BACKGROUND OF THE INVENTION

Field of the Invention

The present invention is related to a structure of righting-up belt of which the tightness adjustment can be more convenient and comfortable and quicker and further meet with the operation of human engineering.

Description of the Prior Art

The lightening-up beltis designed to tighten up and fix something and usually for the use of diving goggles, frogman goggles, snow goggles and diving flipper and disposed between frames on two sides of side goggles or flippers, and the tightness of said belt is adjusted desirably so as to fit to the appropriate position of user's body; for instance, wearing on the user's head or putting on the user's foot.

The conventional tightening-up belt is made of elastic material(such as silica gel or rubber) and integrally moulded as a belt of which the two ends are reversely folded and connected to two sides of a frame of something (such as driving goggles,snow goggles,etc.), and the tightness adjustment thereof is to .rearward tighten up the reversely-folded belt in the positions of connection on two sides, so the tightening elasticity thereof can let the side something tightly put on the appropriate position of user's body.

However, in practice, the foregoing single-piece tightening-up belt remains leaving the following drawbacks to be desired:

1. The tightening-up operation is to rearward stretch (tighten) the reversely-folded belts on two sides. However, such an action of bending the user's hands on the two sides of his hand and stretch the side belts rearward is impeding him from doing so but never handy, and such an operation of undirectionally applying force for tightening up rearward simultaneously on two sides will move the position of wearing the tightening-up belt, for instance, the user will raise his head rearward. The user has to deliberately move his head forward so as to overcome his head moving rearward and to check and balance the rearward tightening force of reversely-folded belt of the tightening-up belt. By so doing, his head can be kept immobile and the tightening-up belt can be tightended rearward by the reversely-folded belt. However, the user has to use his head to keep an action of check and balance in kepping with such a manner of tightening-up operation but it is alien to the handy operation of human engineering;

2. The tightening-up belt is an integral single-piece belt which is rather long and a frictional resistance takes place when the user wears the tightrning-up belt on his head, so when a force is applied to tighten the reversely-folded belts on the two sides of tightening-up belt, the tightening pressure will not ideally, quickly and averagely conveyed to various positions of the tightening-up belt but the two ends thereof are particularly tight, and therefore, it leads to a phenomenon of uneven tightening and uncomfortable wearing; and 3. Normally the two sides of tightening-up belt are disposed with some necessary equipment such as wearing the diving goggles when driving, a snorkel is normally hanged up on a snap ring on one side of the tightening-up belt. However, the reversely-folded on the two sides of conventional tightening-up belt are raising outward to considerably hinder the disposition and operation of the side snap ring and snorkel and relatively impede the operation of tightening and loosending the tightening-up belt.

SUMMARY OF THE INVENTION

The present invention is designed to improve the foregoing defects of conventional tightening-up belt and to offer a novel and bettered structure of tightening-up belt of which the tightness adjustment can be more convenient and comfortable and quicker and further meet with the operation of human engineering.

The present invention is characterized in the following design: the tightening-up belt comprises two belts ,two holding-down plates and one embowed assembly plate, wherein each of the two sides of embowed assembly plate is provided with a slot and a shaft; each of the two belts is provided with a plurality of check strips the fixed end thereof is pivotally fixed on the two sides of a frame of the article to be used, and the free end thereof passes through the slots on the two sides of the embowed assembly plate to be reversely folded around the shaft; and one holding-down plate is installed on the two sides of embowed assembly plate to tighten or loosen the reversely-folded belts. Therefore, the tightening-up belt according to the present invention consisting of two separate belts has an adjustable length and its tightness can be adjusted through laterally pulling toward two outer sides from the position of connecting the two belts (i.e. the center of the whole tightening-up belt), the operation of adjusting the said tightness is quick and handy, and the tightening force thereof can be quickly and averagely conveyed to various positions of the tightening-up belt so that the user feels wearing comfortably. In addition, the reversely-folded part (i.e. the reversely-folded belt) is disposed in the center, namely, when wearing, it is in the rear of the user*s wearing position and will not affect the disposition of other equipment on the two sides of the tightening-up belt.

BRIEF DESCRIPTION OF THE DRAWINGS

FIG. 2 is an exploded view of the tightening-up belt according to the present invention.

DETAILED DESCRIPTION OF THE PREFERRED EMBODIMENTS

Figure 1:
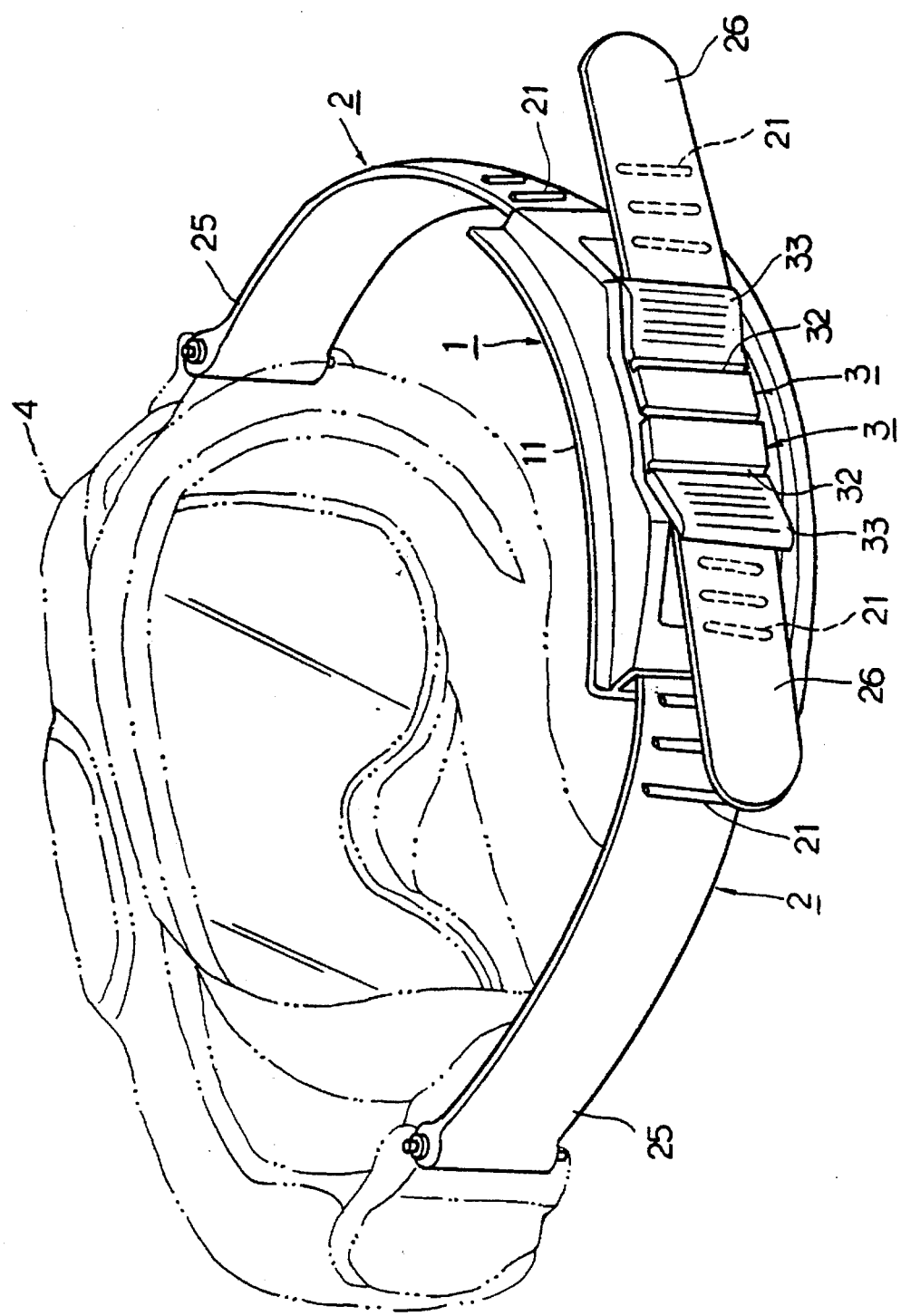
FIG. 1 is an appearance view of the tightening-up belt of the present invention and a scheme thereof when applied to the diving goggles.

As shown in the drawings, the present invention comprises an embowed assembly plate(1),two belts(2),(2)and two holding-down plates(3),(3).

The embowed assembly plate(1) has an embowed plate(11) in comfortably keeping with the embowed exterior of user's wearing position, for instance in keeping with the rear part of the user's head. The two sides on the outer surface of embowed plate(11) are symmetrically provided with a slot (12),(12)respectively,each opening(13),(13) on the inner side of each slot (12),(12)is provided with a shaft(14),(14), and the centeral part of the outer surface of embowed assembly plate(l) is provided with an assembly structure for installing the holding-down plate(3),(3),for instance, a fastening hole(15),(15).

The two belts(2),(2) are made of elastic material such as silica gel or rubber and have a retractable elasticity and a plurality of check strips(21),(21)embossing on the outer surface,each of these check strips (21), (21)has an inclined plane(22) and a acute plane(23), and a thorny edge(24) is formed between the inclined plane(22) and the acute plane(23), and even when these belts(2), (2) are pressed, the side edge(24) is still able to let the belts(2),(2) stretch from a bevel direction but prevent these belts(2),(2)from shrinking back from the direction of acute plane (23). The fixed ends(25),(25) of these belts(2),(2) are respectively pivotally fixed on the two sides of a frame of such article to be used as the diving goggles(4)(as shown in FIG. 1)and the diving flipper(5)(as shown in Fi.4), and the free ends (reversely-folded belts)(26),(26)thereof respectively pass through the slots(12),(12) on the two sides of the embowed assembly plate(1) and then be reversely foloed around the shafts (14),(14) toward the two outer sides so that a part of the free end forms a reversely folded belt(26).(26). After the reversely-folded belt(26),(26) has been reversely foloded, the check strips(21) thereon have also become inward to be caught on the around the shaft(14) together with the check strips(21) on the belts(2),(2) of which the direction remains unchanged.

Figure 3:
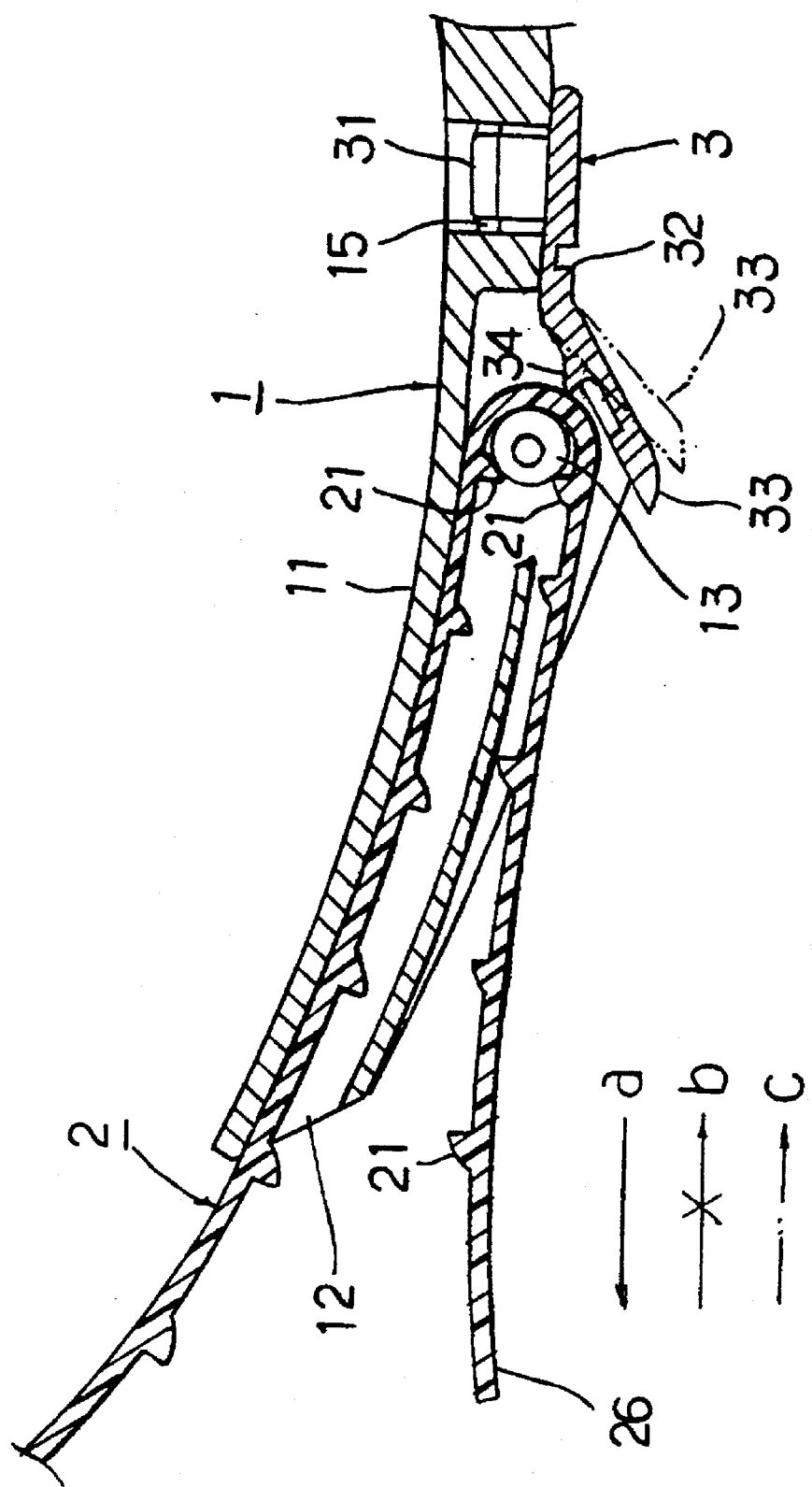
FIG. 3 is a partial section view of the tightening-up belt of the present invention.
Figure 4:
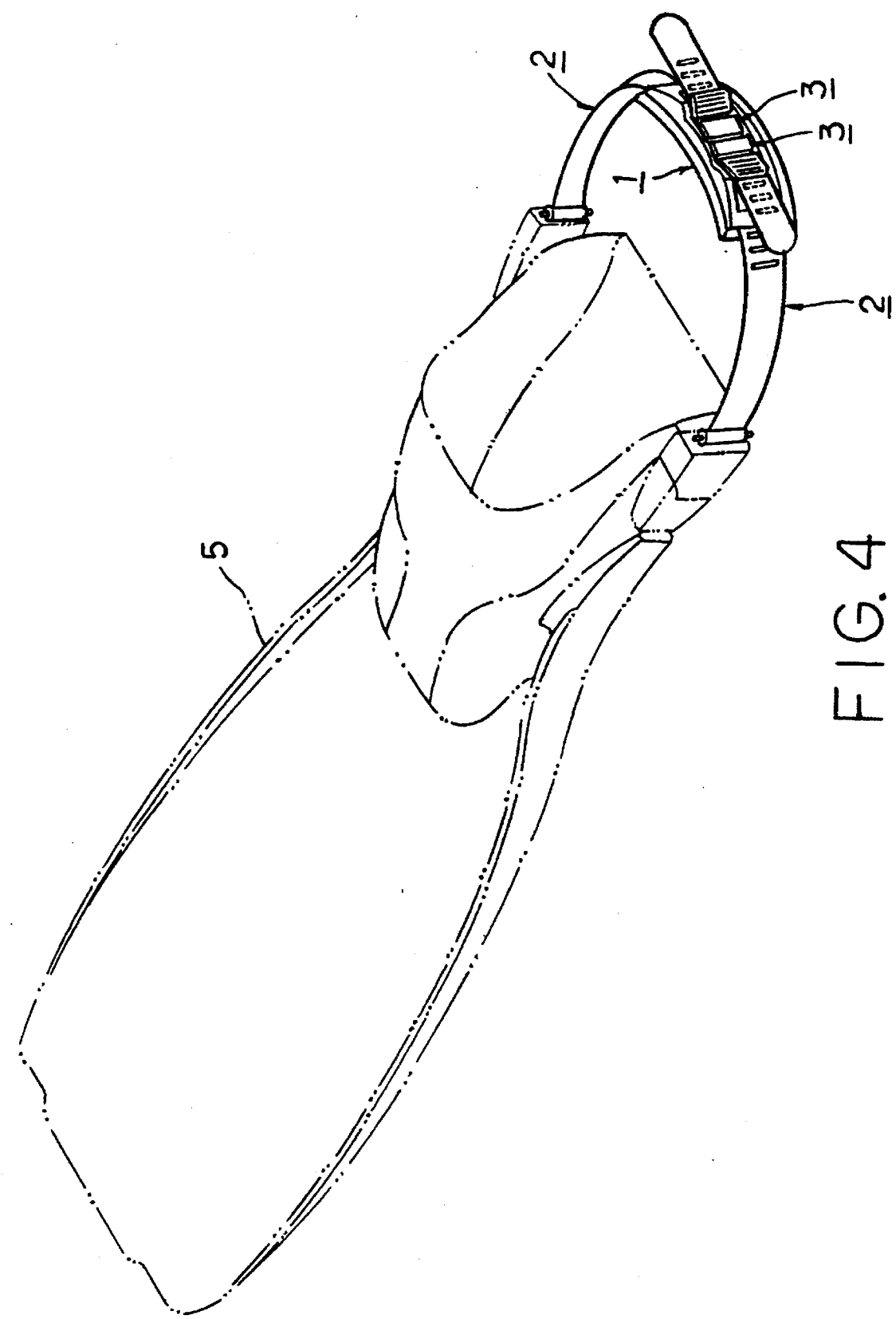
FIG. 4 is an optional view of the present invention applied to the diving flipper.

The foregoing holding-down plates(3),(3) are assembled with the embowed assembly plate(1) through some assembly structure of the former, for instance, each of the holding-down plates(3) is provided with some catch(31).(31) to assemble with the fastening hole(15),(15) on the embowed assembly plate(1), and also provided with an elastic structure which is closing inward and opening outward, for instance, as a spring or recess(32) (32) on the surface of holding-down plate(3),(3) as shown in FIG. 2 so that the outer end portion(operation portion)(33),(33) of recess (32), (32) has an elastic effect of closing inward, opening outward and being pullable and a check strip(34) with the same structure as that on the belts(2),(2) is provided on the inner surface of the operating portion (33),(33). As shown in FIG. 3, normally the operating portion(33),(33) of each holding-down plate(3),(3) is pressed to close inward and in the position of reverse folding of the reversely-folded belt(26), (26) of each belt(2),(2) by the check strip(34) so that the present tightness of each belt(2),(2) is kept from time to time.

When the user wears the present invention together with the articles (such as the diving goggles,diving flippers,etc.)to be used in the wearing positions for use, first to keep them in a more loose state in favor of conveniently wearing them in the wearing positions but the user may simultaneously stretch (tighten)the reversely-folded belts(26),(26) on two sides toward two outer sides respectively until achieving an appropriate tightness. Such an action of stretching outward (as shown by the arrowhead a in FIG. 3) is forward so far as the check strip(34) on the holding-down plate(3) or the check strip(21) on the belt(2) is concerned, thus the reversely-folded belt(26) can be tightened outward to keep such a tightness. Meantime, under the condition of pressing to close inward, the check strip(34) on the holding-down plate(3) prevents the belt(2) from shrinking back inward because such an action of shrinking back inward is reverse so far as the check strip(34) on the holding-down plate(3) or the check strip(21) on the belt(2) is concerned, thus the belt(2) is prevented from shrinking back (as shown by the arrowhead b in FIG. 3) so as to avoid the belt(2) from becoming loose. When the user has finished the use of the present inventtion and the articles attached thereto and intends to remove them from his body, all to do is to pull outward the operating portion(33) of holding-don plate(3) to release the check strip(34)from pressing the reversely-folded belt(26),the belt(2) can restore inward its original more loose state through its restoring force from its orginal tightness (as shown by the dotted-line arrowhead c in FIG. 3) so that the user can conveniently remove them from his body.

According to the present invention, in case of adjusting the tightness of the tightening-up belt, "to pull toward two outer sides" from the position of connecting the two belts(2), (2)(i.e. the central portion of the tightening-up belt as a whole) can tighten the tightening-up belt, and such an operation of tightness adjustment through lateral pull is very handy,quick and convenient without impediment at all and meeting with the handy operation of human engineering. In addition, the present invention consists of two separate belts(2),(2) which or an adjustable length of a whole tihgtening-up belt, and the allocated length of tightness adjustment of each belt(2) is relatively shortened, thus the tightening force of tightness adjustment can be quickly conveyed to various positions of each belt(2) so the user feels wearing comfortable without any phenomenon of uneven distribution of tightness; and the operating portion of tightness adjustment and the reversely-folded belts(26),(26) are at the center of whole tightening-up belt, namely, the rear side of the user's wearing position, it will never affect the disposition of other equipment on the two sides of tightening-up belt nor the tightening and loosening operation of tightening-up belt.

I claim:

1. A tightening-up belt comprising:

an embowed assembly plate as an embowed plate of which the two sides on the outer surface are symmetrically provided with a slot respectively, each opening on the inner side of each slot is provided with a shaft, and the embowed assembly plate is provided with an assembly structure for installing a holding-down plate;

two belts which are made of elastic material and have a retractable elasticity and a plurality of check strips embossing on the outer surface, and when these belts are pressed, these belts still can be pulled outward forward but are prevented from shrinking back reversely; one end (fixed end) of each belt is pivotally fixed on each of two sides of a frame of an article to be used, and another end (free end) thereof passes through each of sots on two sides of embowed assembly plate and then is reversely folded toward two outer sides and around the shaft so that a portion of free end forms a reversely-folded belt to be caught at and around the shaft through the check strips; and two holding-down plates which are assembled with the embowed assembly plate through some assembly structure of the former and have some elastic structure to be closeing inward and opening outward, so the outer end portion (operating portion) of these holding-down plates has an elastic effect of closing inward, opening outward and being pullable, and a check strip with the same structure as that on the two belts is provided on the inner surface of the operating portion and able to tighten or loosen the reversely-folded belt.

2. A tightening-up belt as claimed in claim 1 wherein the embowed assembly plate is provided with some fastening holes to engage with corresponding catches on the holding-down plate.

3. A righting-up belt as claimed in claim 1 wherein the surface of holding-down plate is provided with some recess so that the outer end portion (operating portion) of recess has an elastic effect of closing inward, opening outward and being pullable.

4. A righting-up belt as claimed in claim 2 wherein the surface of holding-down plate is provided with some recess so that the outer end portion (operating portion) of recess has an elastic effect of closing inward, opening outward and being pullable.

* * * * *